(12) United States Patent
Xiong (10) Patent No.: US 11,890,177 B2
(45) Date of Patent: Feb. 6, 2024

(54) POST-PARTUM UNDERGARMENT SYSTEM (71) Applicant: Kia Xiong, Brooklyn Park, MN (US)

(72) Inventor: Kia Xiong, Brooklyn Park, MN (US)

(*) Notice: Subject to any disclaimer, the term of this patent is extended or adjusted under 35 U.S.C. 154(b) by 415 days.

(21) Appl. No.: 16/154,622

(22) Filed: Oct. 8, 2018

(65) Prior Publication Data
US 2019/0125593 A1 May 2, 2019

Related U.S. Application Data

(60) Provisional application No. 62/579,344, filed on Oct. 31, 2017.

(51) Int. Cl.
| | | |
|---|---|---|
| *A61F 13/496* | (2006.01) | |
| *A61F 5/03* | (2006.01) | |
| *A41B 9/14* | (2006.01) | |
| *A41C 1/00* | (2006.01) | |
| *A61F 13/491* | (2006.01) | |
| *A61F 13/14* | (2006.01) | |
| *A41B 9/04* | (2006.01) | |
| *A41C 1/10* | (2006.01) | |
| *A41D 1/21* | (2018.01) | |

(52) U.S. Cl.
CPC .............. *A61F 13/496* (2013.01); *A41B 9/14* (2013.01); *A61F 5/03* (2013.01); *A61F 13/148* (2013.01); *A61F 13/491* (2013.01); *A41B 9/04* (2013.01); *A41C 1/003* (2013.01); *A41C 1/10* (2013.01); *A41D 1/21* (2018.01)

(58) Field of Classification Search
CPC .......... A61F 13/496; A61F 13/42; A61F 5/03; A61F 13/148; A41B 9/14; A41D 1/21; A41C 1/003; A41C 1/08
See application file for complete search history.

(56) References Cited

U.S. PATENT DOCUMENTS

| | | | | |
|---|---|---|---|---|
| 69,659 | A | * | 10/1867 | Hamilton .................. A61F 5/03 450/121 |
| 4,820,296 | A | * | 4/1989 | Masliyah .............. A61F 13/148 604/385.03 |
| 5,613,893 | A | * | 3/1997 | Zagame .................... A41C 1/10 2/311 |
| 5,983,404 | A | | 11/1999 | Jackson |
| 6,062,946 | A | * | 5/2000 | Rosenberg ............... A41C 1/10 450/126 |
| 6,143,240 | A | * | 11/2000 | Jones .................. C22C 33/0207 419/25 |
| 6,146,240 | A | * | 11/2000 | Morris ..................... A41C 1/08 450/97 |

(Continued)

*Primary Examiner* — Catharine L Anderson
*Assistant Examiner* — Arjuna P Chatrathi
(74) *Attorney, Agent, or Firm* — JOHNSON AND PHUNG; Thomas Phung (57) ABSTRACT

A post-partum undergarment system including a brief having a pad and a compression member with a first-wing and a second-wing. The pad is integral to the brief and disposed on an inner layer of the brief in an interspace between the leg holes. The first-wing and the second-wing are configured to wrap around an abdominal region of a woman and secure the compression member in a wrapped-condition. The compression member causes direct compression to the abdominal region of the woman when the brief is worn. The brief is absorbent and disposable for use in postpartum stages.

19 Claims, 5 Drawing Sheets

(56) References Cited

U.S. PATENT DOCUMENTS

| | | | |
|---|---|---|---|
| 7,425,171 B2* | 9/2008 | Maupin | A61F 5/028 |
| | | | 450/96 |
| 8,784,351 B2* | 7/2014 | Dumpson | A41C 1/10 |
| | | | 602/61 |
| 9,622,514 B1 | 4/2017 | Bauer | |
| 2002/0095132 A1* | 7/2002 | Ashton | A61F 13/15 |
| 2005/0014451 A1* | 1/2005 | Wicks | A41C 1/08 |
| | | | 450/155 |
| 2009/0081926 A1* | 3/2009 | Gros | A61F 5/03 |
| | | | 450/155 |
| 2012/0310195 A1* | 12/2012 | Toda | A61F 13/535 |
| | | | 604/385.01 |
| 2013/0131619 A1* | 5/2013 | Ichihara | A61L 15/56 |
| 2013/0239300 A1* | 9/2013 | Denning | A41D 27/00 |
| | | | 2/400 |
| 2014/0148080 A1* | 5/2014 | Hosein | A41C 1/10 |
| | | | 450/155 |
| 2015/0245939 A1* | 9/2015 | Fruscione-Loizides | |
| | | | A61F 13/145 |
| | | | 602/19 |
| 2016/0361190 A1* | 12/2016 | Caden | A41C 1/10 |
| 2017/0143047 A1* | 5/2017 | Howard | A41D 13/0525 |

* cited by examiner

POST-PARTUM UNDERGARMENT SYSTEM

CROSS REFERENCE TO RELATED APPLICATION

The present application is related to and claims priority to U.S. Provisional Patent Application No. 62/579,344 filed Oct. 31, 2017, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. Field of the Invention

The present invention relates generally to the field of undergarments and more specifically relates to an after childbirth post-partum undergarment.

2. Description of Related Art

A postpartum period is the period beginning immediately after the birth of a child and extending for about six weeks. Less frequently used are the terms puerperium or puerperal period. It is the time after birth, a time in which the mother's body, including hormone levels and uterus size, returns to a non-pregnant state. Lochia is postpartum vaginal discharge, containing blood, mucus, and uterine tissue. New mothers may experience heavy bleeding for up to 8 weeks following the birth of her child. In order to combat leaks, some women may choose to wear more loosely unsupportive undergarments with very large pads that can create discomfort when worn under clothes. The large pad may cause shifting while the unsupportive undergarment is unable to keep it in place. Maternity belts may also be worn in order to help keep her loose stomach in place and to prevent the stomach from cramping and jiggling with movements. A suitable solution is desired.

U.S. Pat. No. 5,983,404 to Rosezina Jackson relates to a maternity undergarment and method of use. The described maternity undergarment and method of use includes a garment for giving front abdominal support during the advanced stages of pregnancy which includes a sheet of flexible sheet material having first opposing side edges, the first opposing side edges having opposing leg opening forming notches, defining on one side of the opposing notches a garment front panel and on the other side of the opposing notches a garment rear panel, and defining between the opposing notches a panel interconnection section; the front panel having a support section including support material for supporting the wearer abdominal area; the first opposing side edges including a releasable fastener for interconnecting and for disconnecting the garment front panel and garment rear panel. The garment additionally includes an abdomen support strap extending laterally across and secured to the front panel. A method is provided of placing the above-described garment on a wearer in an advanced stage of pregnancy, including the steps of placing the sheet between the legs of the wearer so that the notches register with and receive the wearer legs; pivoting the front panel upwardly and against the front of the wearer torso and pivoting the rear panel upwardly and against the rear of the wearer torso; bringing the first side edges on the front panel and the first side edges on the rear panel toward each other; and releasably interconnecting the front panel and rear panel first side edges by fastening the fasteners.

BRIEF SUMMARY OF THE INVENTION

In view of the foregoing disadvantages inherent in the known undergarment art, the present disclosure provides a novel post-partum undergarment system. The general purpose of the present disclosure, which will be described subsequently in greater detail, is to provide a comfortable and absorbent undergarment with a sewn-in pad and wrap-around wings, offering much-needed support for a comfortable and active lifestyle.

A post-partum undergarment system is disclosed herein. The post-partum undergarment system includes a brief having a pad and a compression member comprising a first-wing and a second-wing. The brief having the compression member including the first-wing and the second-wing positioned at a waist-portion of the brief. The brief further comprising leg holes. The pad is integral to the brief and disposed on an inner layer of the brief in an interspace between the leg holes. The first-wing and the second-wing are configured to wrap around an abdominal region of a woman. The first-wing and the second-wing further comprise fasteners configured to secure the compression member in a wrapped-condition. The brief is high-waisted allowing for full compression of an abdominal region and excess skin. The compression member causes direct compression to the abdominal region of the woman when the brief is worn. The brief is disposable and provides a postpartum absorbent under garment.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a post-partum undergarment system, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to an undergarment and more particularly to a post-partum undergarment system as used to improve the use of undergarments during a post-partum stage.

Generally, the present invention provides post-partum mothers with a comfortable and absorbent undergarment with a sewn-in pad and wrap-around wings, offering much-needed support for a comfortable and active lifestyle. It includes a sewn-in pad designed to prevent shifting when making movements or while sleeping. It utilizes a quick-absorbing polymer within the sewn-in pad in order to rapidly remove leaks from the undergarments and preventing stains to external clothing. It features a taller waistline, paired with wrap-around wings, in order to support the entire abdominal area including loose skin around the stomach. This allows users to pull on and take off pants similarly to wearing standard undergarments while eliminating the worry of any leaks occurring throughout the day. It offers a less-bulky and form-fitting alternative to standard absorbent undergarments. The present invention effectively eliminates the need to wear an oversized pad, maternity belts and/or unsupportive post-partum undergarment.

Post-partum undergarment system is a form-fitting undergarment for new mother's post-partum. The garment is disposable and features a high brief style with absorbent materials to prevent leaks. Two adhesive wings wrap around the front section of the garment capable of supporting the abdominal area and loose skin around the stomach. The back section can feature a light elastic for additional comfort. Further, the material under the supportive wings is made using a mesh material for keeping the wearer cool. A sewn-in pad can be included designed with a quick-absorbing polymer, offering comfortable support for an active lifestyle. The pad enables women to wear standard clothing without worry of shifting, leaks and/or stains occurring. The padding may be available in various thicknesses and includes a blue/green wet strip on the bottom section to prevent wetness overflow. The garment, overall, features a taller waistline to support the entire abdominal area while still allowing for pants to be pulled on and off in a normal manner. The garment offers much-needed support and comfort for post-childbirth mothers. Post-partum undergarment system can be constructed using polyester, mesh, elastic, and other suitable absorbent materials. The wrap-around wings can feature an adhesive tape in order for the wings to be applied comfortably to the undergarment. The undergarments may be available in small, medium, large, and XL sizes.

Figure 1:
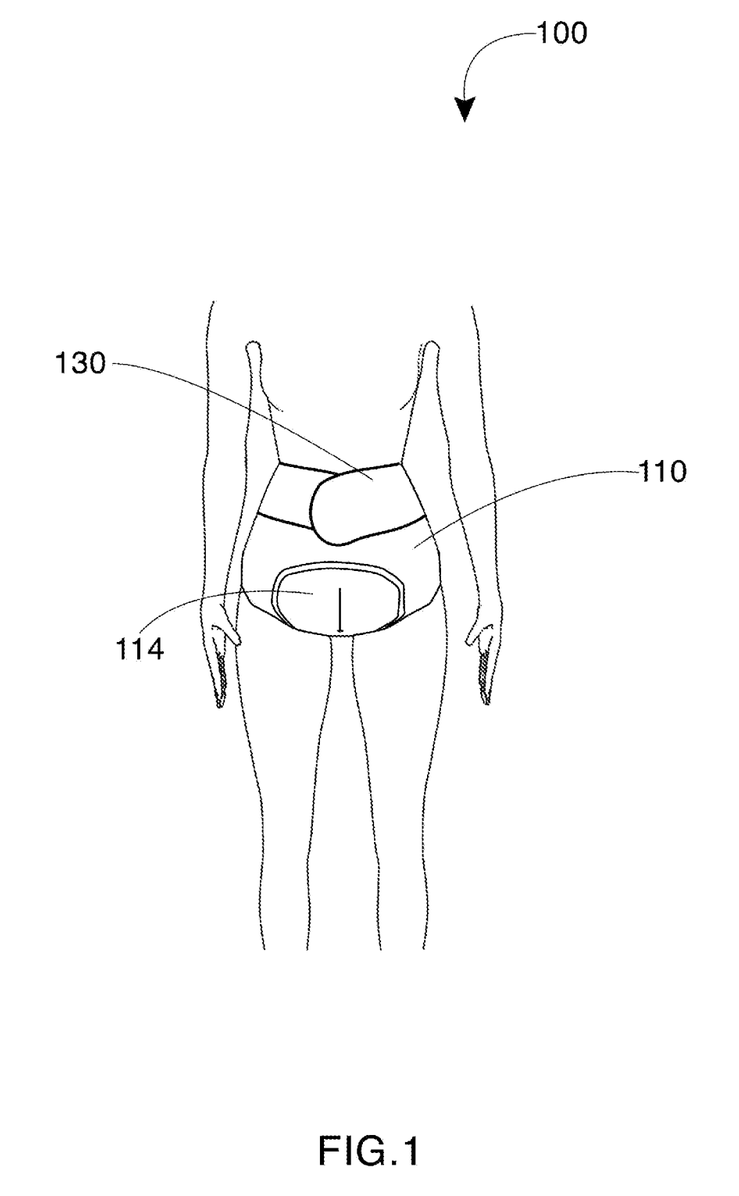
FIG. 1 is a front-perspective view of the post-partum undergarment system during an 'in-use' condition, according to an embodiment of the disclosure.

Referring now more specifically to the drawings by numerals of reference, there is shown in FIGS. 1-5, various views of a post-partum undergarment system 100. FIG. 1 shows a post-partum undergarment system 100 during an 'in-use' condition 150, according to an embodiment of the present disclosure. As illustrated, the post-partum undergarment system 100 may include a brief 110 having a pad 120 and a compression member 130 including a first-wing 132 and a second-wing 138. The brief 110 having the compression member 130 including the first-wing 132 and the second-wing 138 positioned at a waist-portion of the brief 110 with the waist-portion of the brief 110 shown in FIGS. 4 and 5 as being located distal to the pad 120. The brief 110 further comprising leg holes 112. As shown in FIG. 1 the first-wing 132 and second-wing 138 also includes a length and width to allow for the first-wing 132 and second-wing 138 to cover and support the entire abdominal area including loose skin around the stomach of a woman. The pad 120 is integral to the brief 110 and disposed on an inner layer of the brief 110 in an interspace between the leg holes 112. The first-wing 132 and the second-wing 138 are configured to wrap around an abdominal region of a the woman. The first-wing 132 and the second-wing 138 further comprise fasteners 140 configured to secure the compression member 130 in a wrapped-condition. The compression member 130 causes direct compression to the abdominal region of the woman when the brief 110 is worn.

Figure 2:
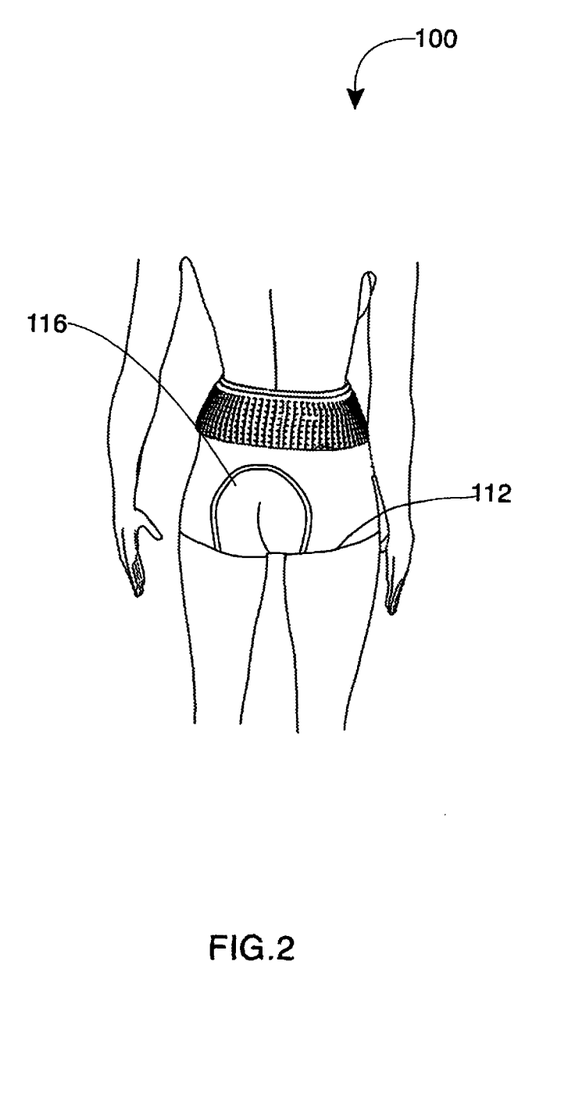
FIG. 2 is a back-perspective view of the post-partum undergarment system of FIG. 1, according to an embodiment of the present disclosure.

FIG. 2 shows a perspective view of the post-partum undergarment system 100 of FIG. 1, according to an embodiment of the present disclosure. As above, the post-partum undergarment system 100 may include the brief 110 having the pad 120 and the compression member 130 including the first-wing 132 and the second-wing 138. The inner layer of the brief 110 includes a liquid permeable material and an outer layer of the brief 110 includes a liquid impervious material. The pad 120 is absorbent for absorbing postpartum discharge. In a preferred embodiment, the pad 120 is sewn-in and integral to the brief 110. The pad 120 extends from a frontal-portion 114 of the brief 110 to a rear-portion 116 of the brief 110 for full coverage. The pad 120 comprises a contoured profile.

Figure 3:
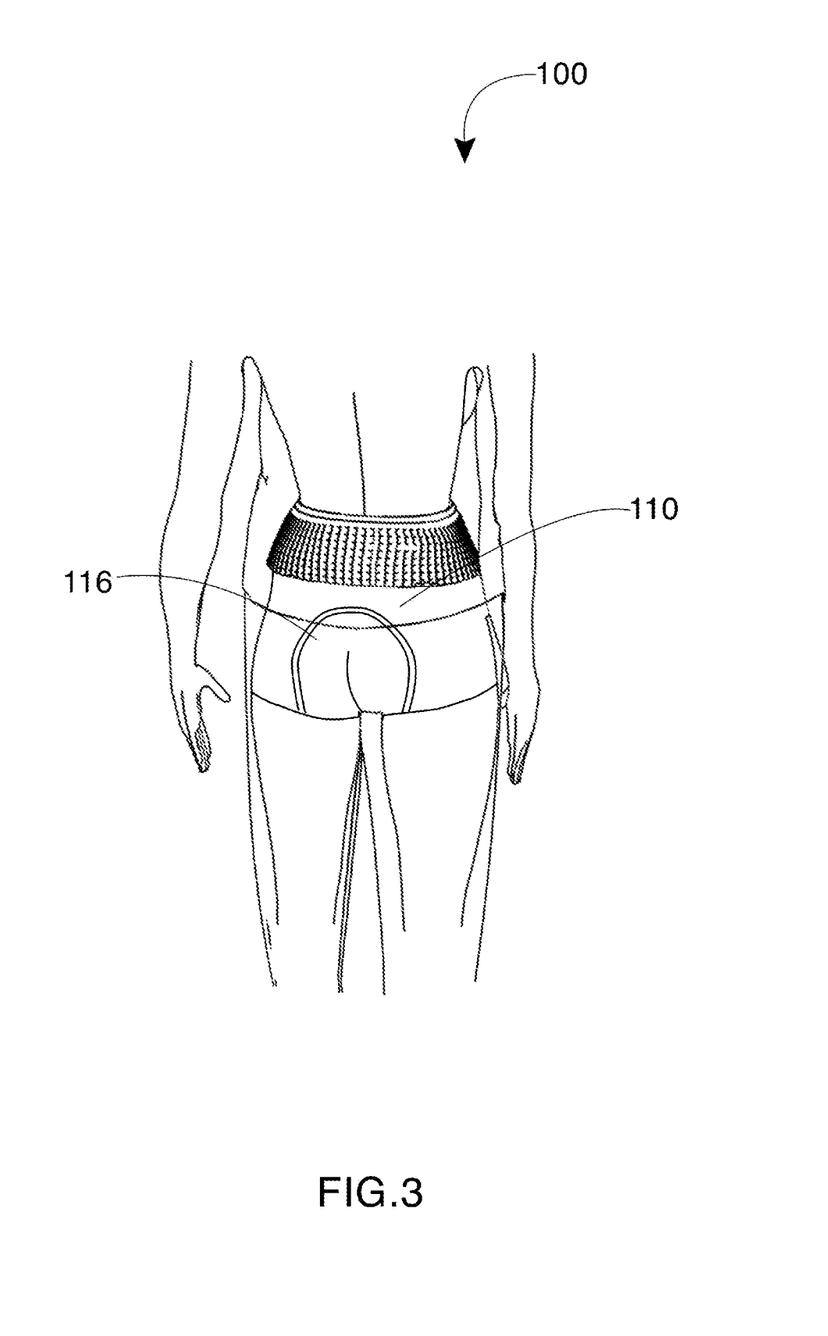
FIG. 3 is a back-perspective view of the post-partum undergarment system of FIG. 1, according to an embodiment of the present disclosure.

FIG. 3 shows a perspective view of the post-partum undergarment system 100 of FIG. 1, according to an embodiment of the present disclosure. As above, the post-partum undergarment system 100 including the brief 110 having the integral pad 120 and the compression member 130 to provide a compression undergarment for use in postpartum phases. In certain embodiments, the brief 110 further comprises an indicator configured to indicate a level of absorbency and prevent overflow. The brief 110 is disposable and comprises disposable, absorbent materials. The brief 110 is flexible and configured to contour a body of the woman during an in-use condition. The brief 110 is high-waisted allowing for full compression of an abdominal region and excess skin. The compression member 130 further comprises elastic material for increased elasticity and comfort. The brief 110 is configured to be worn under clothing discreetly.

Figure 4:
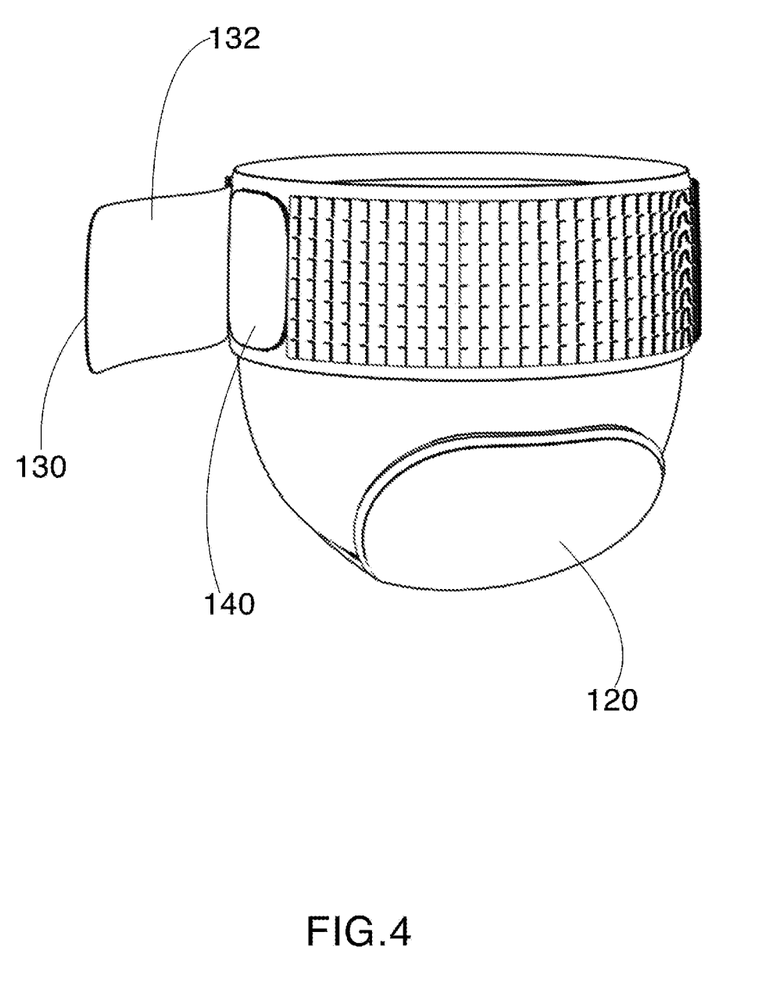
FIG. 4 is a perspective view of the post-partum undergarment system of FIG. 1, according to an embodiment of the present disclosure.
Figure 5:
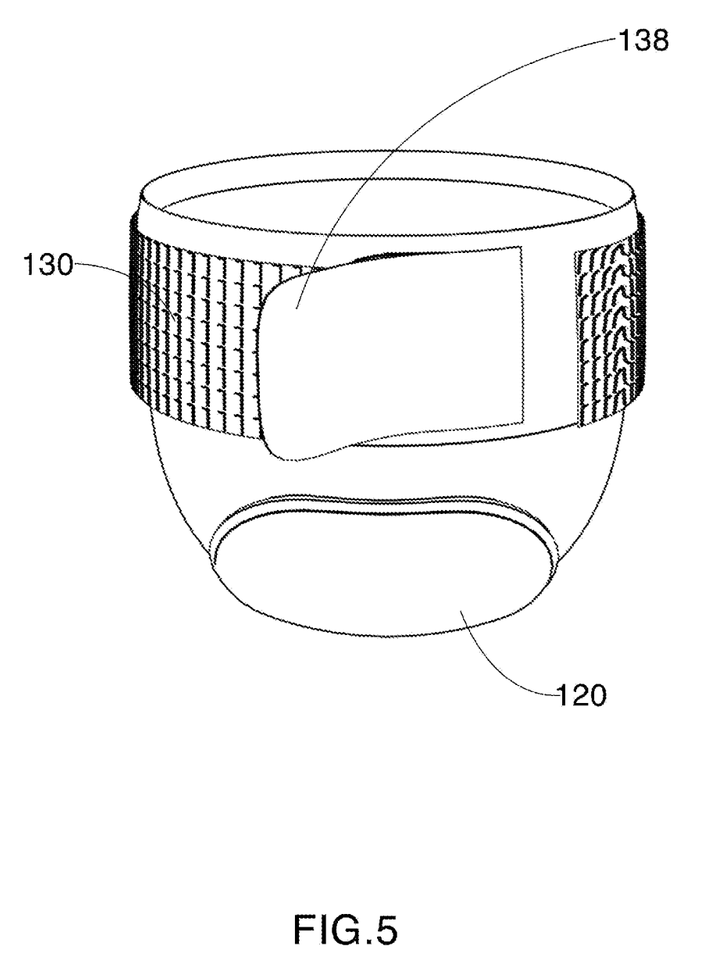
FIG. 5 is a perspective view of the post-partum undergarment system of FIG. 1, according to an embodiment of the present disclosure.

FIGS. 4-5 show perspective views of the post-partum undergarment system 100 of FIG. 1, according to an embodiment of the present disclosure. As above, the post-partum undergarment system 100 comprises the brief 110 having the integral pad 120 and the compression member 130. The compression member 130 further includes the first-wing 132 and the second-wing 138 having fasteners 140 or suitable means for securing the wings in a wrapped condition. The fasteners 140 of the first-wing 132 and the second-wing 138 are releasable. The fasteners 140 may comprise adhesive. The first-wing 132 and the second-wing 138 may further comprise adhesive-tape or other suitable fastening means. The first-wing 132 and the second-wing 138 each include an elongated flexible strap. The first-wing 132 and the second-wing 138 are configured to crisscross and encircle an abdominal region to provide adjustable abdominal support. The first-wing 132 and the second-wing 138 further comprise mesh material for comfort and breathability.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A post-partum undergarment system comprising:
a brief free of leg panels having:
a pad;
a compression member including:
a single pair of wings comprising a first-wing and a second-wing;
wherein said brief having said compression member includes said first-wing and said second-wing positioned at a waist-portion of said brief with said compression member, said first-wing, and said second-wing located on said brief in a spaced and distal condition to said pad with said first-wing and said second wing wrapping directly over an entire front section of said brief, said compression member, said first-wing, and said second-wing having a length and width to extend over an entire abdominal region to support and allow for full compression of said entire abdominal region of a postpartum woman user, said brief further comprising leg holes;
wherein said pad is integral to said brief and disposed on an inner layer of said brief in an interspace between said leg holes;
wherein said first-wing and said second-wing further comprise fasteners configured to secure said compression member in a wrapped-condition and in a binding fashion directly over said abdominal region with at least a portion of said first-wing overlapping a portion of said second-wing; and
wherein said compression member causes direct compression over said abdominal region of said postpartum woman user to maintain the loose stomach of said postpartum woman user in place and to prevent said loose stomach from cramping and jiggling with movements when said brief is worn.

2. The post-partum undergarment system of claim 1, wherein said inner layer of said brief includes a liquid permeable material.

3. The post-partum undergarment system of claim 2, wherein an outer layer of said brief includes a liquid impervious material.

4. The post-partum undergarment system of claim 1, wherein said pad is absorbent.

5. The post-partum undergarment system of claim 4, wherein said pad is sewn-in and integral to said brief.

6. The post-partum undergarment system of claim 1, wherein said pad extends from a frontal-portion of said brief to a rear-portion of said brief.

7. The post-partum undergarment system of claim 6, wherein said pad comprises a contoured profile.

8. The post-partum undergarment system of claim 1, wherein said fasteners of said first-wing and said second-wing are releasable.

9. The post-partum undergarment system of claim 8, wherein said fasteners comprise adhesive.

10. The post-partum undergarment system of claim 1, wherein said first-wing and said second-wing further comprise adhesive-tape.

11. The post-partum undergarment system of claim 1, wherein said first-wing and said second-wing each include an elongated flexible strap.

12. The post-partum undergarment system of claim 11, wherein said first-wing and said second-wing are configured to crisscross and encircle an abdominal region to provide adjustable abdominal support.

13. The post-partum undergarment system of claim 12, wherein said first-wing and said second-wing further comprise mesh material.

14. The post-partum undergarment system of claim 1, wherein said brief is disposable.

15. The post-partum undergarment system of claim 14, wherein said brief is flexible and configured to contour a body of said woman during an in-use condition.

16. The post-partum undergarment system of claim 14, wherein said brief is high-waisted.

17. The post-partum undergarment system of claim 1, wherein said compression member further comprises elastic material for increased elasticity.

18. The post-partum undergarment system of claim 1, wherein said brief is configured to be worn under clothing.

19. A post-partum undergarment system, the post-partum undergarment system comprising:
a brief free of leg panels having:
a pad;
a compression member including:
a single pair of wings comprising a first-wing and a second-wing with said first-wing and second-wing made from a cooling mesh material;
wherein said brief having said compression member includes said first-wing and said second-wing positioned at a waist-portion of said brief with said compression member, said first-wing, and said second-wing located on said brief in a spaced and distal condition to said pad with said first-wing and said second wing wrapping directly over an entire front section of said brief, said compression member, said first-wing, and said second-wing having a length and width to extend over an entire abdominal region to support and allow for full compression of said entire abdominal region of a postpartum woman user, said brief further comprising leg holes;
wherein said pad is integral to said brief and disposed on an inner layer of said brief in an interspace between said leg holes;
wherein said first-wing and said second-wing comprise fasteners configured to secure said compression member in a wrapped-condition and in a binding fashion directly over said entire abdominal region;
wherein said compression member causes direct compression over said abdominal region of said postpartum woman user to maintain the loose stomach of said postpartum woman user in place and to prevent said loose stomach from cramping and jiggling with movements woman user when said brief is worn;
wherein said inner layer of said brief includes a liquid permeable material;

wherein an outer layer of said brief includes a liquid impervious material;
wherein said pad is absorbent;
wherein said pad is sewn-in and integral to said brief;
wherein said pad extends from a frontal-portion of said brief to a rear-portion of said brief; wherein said pad comprises a contoured profile;
wherein said fasteners of said first-wing and said second-wing are releasable; wherein said fasteners comprise adhesive;
wherein said first-wing and said second-wing further comprise adhesive-tape;
wherein said first-wing and said second-wing each include an elongated flexible strap;
wherein said first-wing and said second-wing are configured to crisscross and encircle said abdominal region to provide adjustable abdominal support;
wherein said first-wing and said second-wing further comprise mesh material; wherein said brief is disposable;
wherein said brief is flexible and configured to contour a body of said woman during an in-use condition;
wherein said brief is high-waisted;
wherein said compression member further comprises elastic material for increased elasticity; and
wherein said brief is configured to be worn under clothing.

* * * * *